United States Patent [19]

Ikegami et al.

[11] 4,264,472
[45] Apr. 28, 1981

[54] CATALYST FOR PREPARING POLYETHYLENE

[75] Inventors: Tadashi Ikegami; Hisaya Sakurai; Yoshihiko Katayama; Shigeo Tsuyama; Yukitoshi Iwashita, all of Kurashiki, Japan

[73] Assignee: Asahi Kasei Kogyo Kabushiki Kaisha, Osaka, Japan

[21] Appl. No.: 70,589

[22] Filed: Aug. 29, 1979

[30] Foreign Application Priority Data

Sep. 11, 1978 [JP] Japan .............................. 53-110643
Sep. 14, 1978 [JP] Japan .............................. 53-112362

[51] Int. Cl.³ .............................................. C08F 4/64
[52] U.S. Cl. ............................ 252/429 C; 252/431 R; 526/119; 526/163; 526/127; 526/132; 526/151; 526/159
[58] Field of Search ................... 252/431 R, 429 C

[56] References Cited

U.S. PATENT DOCUMENTS

| | | | |
|---|---|---|---|
| 3,784,481 | 1/1974 | Lassau et al. | 252/429 C X |
| 3,989,878 | 11/1976 | Aishima et al. | 252/431 R X |
| 4,027,089 | 5/1977 | Aishima et al. | 252/429 C X |
| 4,167,493 | 9/1979 | Hsieh | 252/429 C X |
| 4,172,050 | 10/1979 | Gessell | 252/429 C X |

FOREIGN PATENT DOCUMENTS

50100446 2/1977 Japan.
50100940 2/1977 Japan.

*Primary Examiner*—Patrick Garvin
*Attorney, Agent, or Firm*—Sprung, Felfe, Horn, Lynch & Kramer

[57] ABSTRACT

A catalyst for preparing an α-olefin polymer having a broad molecular weight distribution and excellent physical properties, which comprises a solid catalyst component (A) and an organometal compound (B), the solid catalyst component (A) being obtained by reduction with an organomagnesium solution of the thermal decomposition solid product of special titanium compounds.

11 Claims, No Drawings

CATALYST FOR PREPARING POLYETHYLENE

This invention relates to a catalyst for preparing polyethylenes and to a polymerization process employing such a catalyst. The polyethylene produced in the practice of the present invention has a broad molecular weight distribution, excellent homogeneity, and advantageous moldability.

Polyethylene having a broad molecular weight distribution is useful in molding applications such as blow molding and film forming.

In these applications, there is required a polymer having a broad molecular weight distribution and desirable properties such as homogeneity, freedom from gels and high environmental stress cracking resistance (referred to hereinafter as ESCR) as well as predetermined die swelling effects. There have been three methods of broadening the molecular weight distribution. One involves blending at least two polymers having different molecular weights, the second involves multistage polymerization and the third involves polymerization employing a special catalyst. Among these, some are successful to some extent with regard to broadening the molecular weight distribution. However, the homogeneity of the polymers obtained by these methods decreases as the molecular weight distribution increases. The more the moldability of the polymer is improved, the more the surface appearance of the molded articles suffers and the more frequent the occurence of gels on film.

To this end U.S. Pat. No. 3,392,213 discloses a multistage polymerization process designed to improve the surface appearance of molded articles.

Japanese Patent Applications Laid Open Nos. 24291/1977 and 24292/1977 disclose a process for preparing polyethylenes having an improved molecular weight distribution employing special catalysts. However, although the molecular weight distribution of the polymer is broadened to some extent, the polymer becomes inhomogeneous and gels occur on articles molded therefrom. Furthermore, the FR (a measure of the molecular weight distribution described hereinafter) of the obtained polymer is at most in the range of 65 to 85 even in pellets so that the polymer does not satisfy the higher requirements of the marketplace.

However, these problems have been overcome by the novel catalyst of the present invention.

According to this invention there is provided a catalyst for preparing polyethylene, comprising (A) a solid catalyst component and (B) an organometal compound, wherein the solid catalyst component (A) is prepared by reducing a solid (1) with a solution of an organomagnesium compound (2). The solid (1) is obtained by the thermal decomposition of (i) a polytitanate of the general formula RO$-(-Ti(OR)_2O-)_n$R and (ii) a titanium tetrahalide TiX$_4$, or by the thermal decomposition of (iii) a titanium compound of the general formula Ti(OR)$_a$X$_{4-a}$. The solid (1) includes a halogen and titanium atom in the atomic ratio of $0 < X/Ti \leq 2$. In the general formulae, R may be the same or different and is a sec- or tert-hydrocarbon group having at least 3 carbon atoms, n is an integer of at least 2, X represents a halogen atom and a is a positive number from 0 to 1, viz. $0 < a \leq 1$.

Catalysts disclosed in Japanese Patent Applications Laid Open Nos. 24291/1977 and 24292/1977 are mixtures comprising a solid supporting a titanium compound on an inorganic magnesium compound (a carrier) and a titanium oxyhalide. There are two major differences between these mixed catalysts and the catalyst of the present invention.

According to the present invention, there is used a solution of an organomagnesium compound or complex having a Mg—C bond, in contradistinction to the inorganic magnesium compound used in the mixed catalysts. This catalyst component of the present invention is prepared by the reduction of a solid having an atomic ratio of $0 < X/Ti \leq 2$ with the organomagnesium solution and is different from merely supporting the inorganic magnesium compound. Owing to these differences, the obtained results illustrated hereinbelow in more detail in the Examples and Comparative Examples are also different as shown by the following Table:

TABLE

| | FR (breadth of the M.W. distribution) | | Amount of Gel (a relative value per Kg of a film) | ESCR (hour) |
| --- | --- | --- | --- | --- |
| | Polyethylene Powder | Polyethylene Pellet | | |
| Present Invention | 75–95 | 100–140 | <50 | >24 |
| Jap. Pat. Appln. Laid Open No. 24291/1977 | 45–65 | 60–85 | >10,000 | 1 |
| Jap. Pat. Appln. Laid Open No. 24292/1977 | 45–65 | 70–85 | >10,000 | 2 |

The polymer obtained in the present invention has excellent properties such as broad molecular weight distribution, good homogeneity, high rigidity and high environmental stress cracking resistance (ESCR). Blow molded bottles have a smooth surface; blown films contain no gel and have good homogeneity. The polymer is also useful for large blow molded articles and pipes due to its high rigidity, ESCR and impact strength.

As described in the examples hereinbelow, polymer prepared by using the present catalyst shows a very large die swell. For this reason, when it is used as a modifier for a polymer having a low die swell, it is easily possible to improve on the moldability. For example, by the addition of the present polymer to a polymer having a low die swell prepared by a Ziegler type catalyst, it is possible to attain as high a die swell as exhibited by polyethylene prepared by a Phillips type catalyst. Furthermore, the instant polymer shows high elasticity on melting (melt-tension). As a result, it is also useful as a modifier for the improvement of bubble-stability in film blowing and of pinch-off stability in blow molding.

The polymer powder shows an extremely high bulk density and has few fine particles so that polymerization and handling of the polymer are facilitated.

DETAILED DESCRIPTION OF THE PREFERRED EMBODIMENTS

Each of the component materials and reaction conditions employed for the preparation of the catalyst will be described hereinafter in detail.

The thermally decomposed product (1) which is used as one of the raw materials of the catalyst is prepared by the following two methods and each includes halogen and titanium in the atomic ratio of $0 < X/Ti \leq 2$ and performs the same in polymerization.

One method of obtaining the solid (1) is by thermal decomposition of (i) a polytitanate and (ii) a titanium tetrahalide.

The polytitanate (i) used in this reaction is represented by the general formula $RO(Ti(OR)_2-O)_nR$, wherein R and n have the definitions given above. Thus, R each independently is a secondary or tertiary hydrocarbon group having at least 3 carbon atoms, e.g. an aliphatic, alicyclic or aromatic hydrocarbon group. Exemplary groups include isopropyl, sec- or tert-butyl, amyl, hexyl, heptyl, octyl, decyl, dodecyl, hexadecyl, cyclohexyl, phenyl, and the like. A preferred radical is a sec- or tert-aliphatic hydrocarbon having 3 to 6 carbon atoms. n is at least 2 and preferably 2 to 20. Such polytitanates may be prepared by the known oligomerization of $Ti(OR)_4$ and are commercially available.

Titanium tetrahalides (ii) of the formula $TiX_4$ wherein X is a halogen include titanium tetrafluoride, titanium tetrabromide, titanium tetraiodide, and preferably titanium tetrachloride.

The thermal decomposition of (i) a polytitanate and (ii) a titanium tetrahalide is carried out in the presence or absence of an aliphatic, alicyclic or aromatic medium at a temperature of at least about 50° C. In this reaction, the mole ratio and the concentration of the compounds (i) and (ii) and the reaction temperature are important in order to obtain a good product and to carry on the reaction smoothly. A preferred mole ratio of Ti in $TiX_4$ (ii) to Ti in polytitanate (i) is 3 or more. The concentration of the two compounds is at least 1 mol/l, preferably at least 4 mols/l. The temperature is at least about 40° C., preferably at least about 80° C. and more preferably about 100° to 200° C. The reaction also can be carried out in the presence of a solid carrier such as metal oxide (e.g., silica, alumina, silica/alumina, zirconia, magnesia, and the like), a metal chloride (e.g. magnesium chloride, manganese chloride, and the like) or a metal hydroxide (e.g., titanium hydroxide, and the like.

After the reaction, a solid product (1) of the thermal decomposition is separated from the liquid phase, and, preferably washed with an inert hydrocarbon. The OR group contained in the starting material $RO(Ti(OR)_2-O)_nR$ is substantially absent in the solid. The solid obtained contains halogen and titanium in the mole ratio $0 < X/Ti \leq 2$, preferably $1 \leq X/Ti \leq 1.8$, the value being controlled by the choice of reaction conditions, mole ratios, concentration of the starting material, and the like.

Another method of obtaining the thermal decomposition product (1) is by thermally decomposing a titanium compound (iii) of the general formula $Ti(OR)_aX_{4-a}$ wherein R has the same meaning as recited in connection with the polytitanate (i).

As the halogen atom X, any of the fluorine, chlorine, bromine and iodine are suitable, chlorine being preferred. The value of a ranges from more than zero to not more than 1, preferably not more than 0.75. These titanium compounds (iii) which may be employed are synthesized by known methods or by the reaction of titanium tetrahalide and an alcohol or a metal alkoxide such as aluminum isopropoxide under thermal decomposition conditions.

The thermal decomposition of the titanium compound (iii) is conducted in the same manner as described hereinbefore, and the product obtained has the same composition as the thermal decomposition product prepared from (i) the polytitanate $R(Ti(OR)_2-O)_nR$ and (ii) the titanium tetrahalide $TiX_4$.

Further details will now be provided of the organomagnesium solution (2) that is used as a reducing agent for the thermal decomposition product (1) in order to obtain the solid catalyst component (A).

As the magnesium component of the organomagnesium solution, there can be employed a magnesium compound or complex having a magnesium-carbon bond. A preferred solution is an inert hydrocarbon solvent containing a soluble organomagnesium compound or complex.

As the inert hydrocarbon-soluble organomagnesium compound there may be used an alkoxy, aryloxy or siloxy magnesium compound represented by the general formulas $R^1Mg(OR^2)$ and $R^3Mg(OSiR^4R^5R^6)$ wherein $R^1$, $R^2$ and $R^3$ are hydrocarbon groups, preferably alkyl groups, $R^4$, $R^5$ and $R^6$ are hydrocarbon groups or one or two of them may be convertible to hydrogen, or a dialkylmagnesium having sec- or tert-alkyl groups, an assymmetric dialkylmagnesium or a long chain dialkylmagnesium.

Exemplary magnesium compounds include n-$C_4H_9Mg(OC_3H_7)$, n-$C_4H_9Mg(OC_4H_9)$, n-$C_4H_9Mg(OC_5H_{11})$, n-$C_4H_9Mg(OC_6H_{13})$, n-$C_4H_9Mg(OC_8H_{17})$, $C_5H_{11}Mg(OC_4H_9)$, $C_6H_{13}Mg(OC_3H_7)$, n-$C_4H_9Mg(OSiH.CH_3.C_4H_9)$, n-$C_4H_9Mg(OSiH.C_6H_5.C_4H_9)$, $(sec-C_4H_9)_2Mg$, $(tert-C_4H_9)_2Mg$, $C_2H_5Mgn-C_4H_9$, $sec-C_4H_9Mgn-C_4H_9$ and $iso-C_3H_7Mgn-C_4H_9$.

A suitable organomagnesium complex is a compound represented by the general formula $R^7_iMgX_{2-i}.JD$, wherein $R^7$ is a hydrocarbon group; X is a halogen atom, i is 1 to 2; D represents an electrondonor-organo compound; and j is 1 to 2. Preferably $R^7$ is alkyl and X is chlorine. Exemplary base compounds exclusive of D include, for example, $(CH_3)_2Mg$, $(C_2H_5)_2Mg$, $(C_3H_7)_2Mg$, $(C_4H_9)_2Mg$, $(C_5H_{11})_2Mg$, $(C_6H_{13})_2Mg$, $(C_8H_{17})_2Mg$, $CH_3MgCl$, $C_3H_7MgCl$, $C_4H_9MgCl$, $C_6H_{13}MgCl$, $C_8H_{17}MgCl$, $C_4H_9MgBr$, $C_4H_9MgI$, and mixtures thereof. As the electrondonor-organo compound are used ethers, siloxanes, amines, nitriles, ketones, aldehydes and organic esters such as diethyl ether, dipropyl ether, dibutyl ether, diphenyl ether, tetrahydrofuran, methylpropyl ether, ethylene glycol diethyl ether, diethylene glycol dimethyl ether, propylene oxide, hexamethyl disiloxane, symmetrical dihydrotetramethyl disiloxane, pentamethyl trihydro trisiloxane, cyclic methyl hydro tetrasiloxane, methyl hydro polysiloxane, triethyl amine, tributyl amine, pyridine, ethylene diamine, acetonitrile, propionitrile, acrylonitrile, benzylnitrile, benzonitrile, acetone, methyl ethyl ketone, diphenyl ketone, acetyl acetone, acetaldehyde, ethyl acetate, butyl benzoate, and the like.

A third group of organomagnesium compounds is an organomagnesium complex represented by the general formula $M_\alpha Mg_\beta R^8_p R^9_q Y^1_r Y^2_s$, wherein M is a metal atom selected from aluminum, zinc, boron, lithium and beryllium, $R^8$ and $R^9$ are the same or different hydrocarbon groups having 1 to 10 carbon atoms, $Y^1$ and $Y^2$ are the same or different groups selected from $OR^{10}$, $OSiR^{11}R^{12}R^{13}$, $NR^{14}R^{15}$ and $SR^{16}$, wherein $R^{10}$ and $R^{16}$ are hydrocarbon groups having 1 to 10 carbon atoms; $R^{11}$, $R^{12}$, $R^{13}$, $R^{14}$ and $R^{15}$ are hydrogen or hydrocarbon groups having 1 to 10 carbon atoms; $\alpha$ and $\beta$ are numbers greater than zero; p, q, r and s are zero or numbers greater than zero having the relationship $\beta/\alpha \geq 0.5$, $p+q+r+s=m\alpha+2\beta$ and $0 \leq (r+s)/(\alpha+\beta) \leq 1.0$, wherein m is the valence of M.

Of these groups and numbers, the preferred hydrocarbon groups represented by $R^8$ and $R^9$ are alkyl, cycloalkyl and aryl groups such as methyl, ethyl, propyl, butyl, amyl, hexyl, decyl, cyclohexyl, phenyl, and the like. An alkyl group is especially preferred as $R^8$. The ratio of $\beta/\alpha$ is preferably in the range of 0.5 to 20, especially 0.5 to 10.

These organomagnesium compounds and complexes are easily prepared by using the method disclosed in patents such as U.S. Pat. Nos. 4,004,071, 4,027,089, 3,989,878 and 4,120,883, and the documents such as Annalen der Chemie, 605, 93–97 (1957), J. Chem. Soc., 1964, 2483–85, Chemical Communication, 1966, 559, and J. Org. Chem., 34, 1116 (1969).

All organomagnesium solutions described above are suitable in the practice of the present invention, but the inert hydrocarbon solvents are preferred. Most preferred is an inert hydrocarbon solution containing the complex $M_\alpha Mg_\beta R_p^8 R_q^9 Y_r^1 Y_2^2$. As an inert hydrocarbon, it is recommended to use an aliphatic hydrocarbon such as hexane or heptane, an aromatic hydrocarbon such as benzene or toluene or an alicyclic hydrocarbon such as cyclohexane or methylcyclohexane. An aliphatic or alicyclic hydrocarbon is preferred.

Details will now be given of the synthesis of the solid catalyst component (A) by the reduction of the thermal decomposition product (1) with the organomagnesium solution (2).

The reduction is conducted in an inert hydrocarbon medium such as an aliphatic hydrocarbon (i.e., hexane, heptane), an aromatic hydrocarbon (i.e., benzene, toluene, xylene) or an alicyclic hydrocarbon (i.e., cyclohexane, methyl cyclohexane), at a temperature of about $-80°$ to $150°$ C., preferably $-30°$ to $100°$ C. As for the molar ratio of the two compounds, the mole ratio of Mg, in the solution of the magnesium compound or complex (2), to Ti, in the thermal decomposition product (1) is in the range of 0.05 to 50, and preferably in the range of 0.1 to 5.

After the reduction, it is preferred that the solid component obtained is isolated and washed with an inert hydrocarbon to obtain the solid catalyst component (A).

The organometal compound (B) which is used with the solid catalyst component (A) is a compound of a metal of Groups I to III of the Periodic Table, especially an organoaluminum compound or an organomagnesium complex. As organoaluminum compounds, those represented by the general formula $AlR_t^{17}Z_{3-t}$, wherein $R^{17}$ is a hydrocarbon group having 1 to 20 carbon atoms, Z is a member selected from hydrogen, halogen, alkoxy, aryloxy and siloxy, and t is 2 to 3, are used individually or as a mixture. In the above formula, hydrocarbon groups having 1 to 20 carbon atoms represented by $R^{17}$ include aliphatic hydrocarbons, aromatic hydrocarbons and alicyclic hydrocarbons.

Specifically, for example, triethylaluminum, tri-n-propylaluminum, triisopropylaluminum, tri-n-butylaluminum, triisobutylaluminum, trihexylaluminum, trioctylaluminum, tridecylaluminum, tridodecylaluminum, trihexadecylaluminum, diethylaluminum hydride, diisobutylaluminum hydride, diethylaluminum ethoxide, diisobutylaluminum ethoxide, dioctylaluminum butoxide, diisobutylaluminum octyloxide, diethylaluminum chloride, diisobutylaluminum chloride, dimethylhydrosiloxyaluminum dimethyl, ethymethylhydrosiloxyaluminum diethyl, ethyldimethylsiloxyaluminum diethyl, aluminum isoprenyl, and the like, or mixtures thereof are recommended.

A combination of these alkylaluminum compounds with the above mentioned solid catalyst component (A) provides a highly active catalyst, and especially trialkylaluminum and dialkylaluminum hydride are preferred because they show the highest activity.

As organomagnesium complexes, there may be used the same complexes $M_\alpha Mg_\beta R_p^8 R_q^9 Y_r^1 Y_s^2$ as employed in the reduction. Among them, complexes wherein M is aluminum are preferred.

The organometal compound (B) and the solid catalyst component (A) may be added to the polymerization system separately or may be mixed prior to the polymerization.

The amount of the organometallic compound (B) preferably ranges from about 1 millimol to 3000 millimols per gram of the solid catalyst component (A).

DETAILED DESCRIPTION OF THE POLYMERIZATION

Olefins polymerized by using the present catalyst may be $\alpha$-olefins, especially ethylene, or diolefins, i.e. dienes. Further, the present catalysts may be employed for copolymerizing ethylene and other monoolefins such as propylene, butene-1, hexene-1 and the like, and dienes such as butadiene, isoprene, and the like.

As for the polymerization method, there may be employed the usual suspension-, solution- and gas phase-polymerizations. In the cases of suspension- and solution-polymerizations, the catalyst is introduced into a reactor together with a polymerization medium, e.g., aliphatic hydrocarbon such as hexane, or heptane; aromatic hydrocarbon such as benzene, toluene or xylene; or alicyclic hydrocarbon such as cyclohexane or methylcyclohexane, and, ethylene is added under a pressure of 1 to 50 Kg/cm$^2$ in an inert atmosphere and allowed to polymerize at a temperature from about room temperature to about 150° C.

For gas phase-polymerization, it is possible to carry out polymerization under an ethylene pressure of 1 to 50 Kg/cm$^2$ and a temperature from about room temperature to about 120° C., using a fluidized bed, moving bed or mixing with a stirrer to provide better contact between the ethylene and catalyst.

There may be employed single stage polymerization or multistage polymerization.

The present catalyst makes it possible to prepare a polymer whose molecular weight distribution is sufficiently broad, even in one stage polymerization. Furthermore, when multiple stage polymerization is effected in at least two polymerization zones having different polymerization conditions, by using the present catalyst it is possible to prepare a polymer whose molecular weight distribution is much broader.

In order to control the molecular weight of the polymer, it is also possible to add hydrogen, a halogenated hydrocarbon or an organometallic compound which can cause chain transfer.

Furthermore, it is also possible to carry out the polymerization with the addition of a titanate to control the density of the polymer, in combination with the polymerization methods as described above.

The following examples of preferred embodiments further illustrate the principle and practice of the invention:

In the following example,

MI is the melt index measured according to ASTM D-1238, wherein temperature and load are 190° C. and 2.16 Kg, respectively;

FR is the quotient of the melt high-load index measured at a temperature of 190° C. and a load of 21.6

Kg divided by MI; the larger the quotient, the broader is the molecular weight distribution;

Die swell is the weight in grams of 20 cm of a parison extruded from a die having an outside diameter of 16 mm and an inside diameter of 10 mm;

The number of gels is the number found per 1 Kg of film; and

ESCR (Environmental Stress Craking Resistance) is the number of hours at 50% failure point, measured according to ASTM D-1693. Specimen thickness and bath temperature are 2 mm and 80° C., respectively. The test reagent is Neugen® (nonylphenolpolyoxyethylene).

EXAMPLE 1

(I) Synthesis of the solid catalyst component

In a 300 ml flask equipped with a reflux condenser, a stirrer and a dropping funnel from which moisture and oxygen had been removed by replacement with dry nitrogen, there was placed 700 mmol of titanium tetrachloride. In the dropping funnel, 100 mmol (based on titanium atom) of isopropyl titanate decamer (prepared by Nippon Soda Co., Ltd.) iso-$C_3H_7$-O-[Ti(O-iso-$C_3H_7)_2$-O-]$_{10}$iso-$C_3H_7$ was placed. After the flask was heated at 110° C., the titanate was added dropwise over one hour through the dropping funnel with stirring under a nitrogen atmosphere. The mixture was reacted further for two hours. With the progress of the reaction, a gas was evolved and then a light ocher solid was formed. The solid portion was isolated, washed with n-hexane and dried to give 26.9 g of (1) the solid. The contents of Ti and Cl in the solid (1) were 36.3 wt.% and 38.0 Wt.%, respectively, which corresponded to an atomic ratio of Cl/Ti of 1.41. The content of $OiC_3H_7$ was less than 0.1 wt.%.

Ten mmol (based on titanium) of the solid (1) and 50 ml of n-hexane were charged to a 100 ml flask equipped with a dropping funnel and a stirrer, having been fully purged with nitrogen, slurried and cooled to −10° C. To the slurry, 20 ml of a hexane solution containing 10 mmol (based on magnesium atom) of the organomagnesium complex $AlMg_{6.0}(C_2H_5)_{2.9}$ (n-$C_4H_9)_{12.1}$ was added dropwise over 30 minutes with stirring at −10° C. After dropping, the mixture was allowed to react at 25° C. for one hour. The solid catalyst component (A) formed was isolated, washed and dried. Its color was nearly black.

(II) Polymerization

In a 30 l autoclave, evacuated and then nitrogen-filled, were placed 800 mg of the solid catalyst component (A) synthesized in (I) and 7.5 mmol of triisobutyl aluminum with 15 l of hexane. While keeping the temperature of the autoclave at 85° C., hydrogen was added up to 5.0 Kg/cm². Then ethylene was added up to a total gauge pressure of 10 Kg/cm². While maintaining the total gauge pressure of 10 Kg/cm² by adding ethylene, the polymerization was carried out for 4 hours. The yield of the polymer was 6.5 Kg. In the powder form of the obtained polymer, MI, FR, true specific gravity and bulk density were 0.39, 85, 0.965 and 0.42, respectively.

(III) Moldability

The polymer obtained was pelletized with an extruder having a screw of 40 mm diameter. The pellet had a MI of 0.24 and a FR of 130. The effect of die swell of the present polymer was shown in Table 1 with data for conventional polyethylene Hi-Zex 6200B (prepared by Mitsui Petrochemical Industries, Ltd.) and the mixture of 9 parts of said 6200B and 1 part of the present polyethylene.

TABLE 1

|  | Polyethylene of Example 1 | Conventional polyethylene Hi-Zex 6200B | Blended Polyethylene Example 1/6200B = 1/9 |
|---|---|---|---|
| die swell | 64 | 35 | 40 |

The polyethylene obtained in Example 1 itself had a large die swell, and markedly improved the die swell of another polymer having a small die swell.

Bottles molded therefrom had a good surface appearance and film therefrom showed gel numbers of less than 50. This polymer was excellent in ESCR with a value of more than 24 hours.

EXAMPLE 2

(I) Synthesis of the solid catalyst component

A solid (1) was prepared by the same method as described in (I) of Example 1, except that 1100 mmol of an octane solution containing 4 mol/l of titanium tetrachloride was used.

The titanium and chlorine content in the solid (1) were 37.8 wt.% and 42.0 wt.% respectively which corresponded to an atomic ratio of Cl/Ti of 1.50.

As in (I) of Example 1, 10 mmol (based on titanium atom) of the solid (1) and the hexane solution of 5 mmol (based on magnesium atom) of the organomagnesium complex $AlMg_{3.0}(C_2H_5)_{3.1}$ (n-$C_4H_9)_{5.9}$ were reacted at −20° C. for 6 hours, one hour for the dropwise addition and further reaction for 5 hours, to obtain the solid catalyst component (A).

(II) Polymerization

Polymerization was carried out under the same polymerization conditions as in Example 1, using 800 mg of the solid catalyst component (A) obtained above and 30 mmol of aluminum trinormalbutyl. 6 Kg of polyethylene was obtained. The polyethylene powder showed MI of 0.35, FR of 87, a true specific gravity of 0.962 and a bulk density of 0.45.

The polymer obtained was pelletized with an extruder having a screw of 40 mmφ. The pellet showed MI of 0.22 and FR of 135. The die swell of the pellet is shown in Table 2 with the data for another polyethylene. Bottles molded with polyethylene obtained from this example had a good surface appearance. The numbers of gels was less than 50 per Kg of film from the polyethylene. The pellet was excellent in ESCR with a value of 24 hours.

TABLE 2

|  | Polyethylene obtained in Example 2 | Conventional Polyethylene Hi-Zex 6200B | Blended Polyethylene Example 2/6200B = 15/85 |
|---|---|---|---|
| die swell | 63 | 35 | 42 |

EXAMPLE 3

(I) Synthesis of the solid catalyst component

The solid (1) was prepared by the same method as described in Example 1 (I), except that 500 mmol of an octane solution containing 4 mol/l of titanium tetrachloride was used and that as a polytitanate there was employed an octane solution of 4 mol/l (based on titanium atom) of isopropyl titanate pentamer. The solid (1) obtained had titanium and chlorine contents of 34.2 wt.% and 34.1 wt%, respectively, and a mol ratio of Cl/Ti of 1.35.

The solid catalyst component (A) was also prepared by the same procedure as described in Example 1, (I) except that 10 mmol (based on titanium atom) of the solid (1) obtained above and a hexane solution containing 20 mmol (based on magnesium atom) of an organomagnesium having the composition $ZnMg_{2.0}(C_2H_5)_{2.0}(C_6H_{13})_{4.1}$ were reacted at 40° C. for 1.5 hours, the dropwise addition taking 30 minutes and further reaction 1 hour.

(II) Polymerization

Polymerization was carried out under the same conditions as described in Example 1, by using 800 mg of the solid catalyst component (A) obtained above and 3.75 mmol of aluminum triethyl. 5.5 Kg of polymer was obtained. The polymer powder showed MI of 0.15, FR of 93, a true specific gravity of 0.960 and a bulk density of 0.44.

(III) Moldability

Die swell of the polymer obtained was measured by the same method as in Example 1 and is shown in Table 3 with the data for another polymer. The film prepared with the present polymer had gel numbers of less than 50 and was excellent in film-tenacity. At the film-mold, there was good bubble-stability.

TABLE 3

|  | Polyethylene of Example 3 | Conventional Polyethylene Hi-Zex 7000F | Blended Polyethylene Example 3/7000F = 15/85 |
|---|---|---|---|
| die swell | 59 | 31 | 38 |

COMPARATIVE EXAMPLE A

A catalyst was prepared in accordance with the disclosure of Japanese Patent Application Laid Open No. 24292/1977 and polymerization using said catalyst was effected for comparison with the present catalyst.

(I-a) Solid component (a)

The solid (1) of instant Example 1 was used as the solid component (a).

(I-b) Synthesis of solid component (b)

In a 500 ml flask equipped with a condenser, under a nitrogen flow, 20 g of $Mg(OC_2H_5)_2$ was charged and then 200 ml of $TiCl_4$ was added. The mixture was reacted for 2 hours at 130° C. After the reaction, the mixture was cooled to room temperature. The solid part was isolated, washed with purified n-hexane and dried to obtain the solid component (b).

(II) Polymerization

Polymerization was carried out under the same polymerization conditions as in Example 1, by using 720 mg of the solid component (a), 80 mg of the solid component (b) and 15 mmol of aluminum triisobutyl. 6.4 Kg of polyethylene was obtained. The polyethylene powder had MI of 0.45, FR of 55, a true specific gravity of 0.965 and a bulk density of 0.20.

(III) Moldability

The polymer obtained was pelletized with an extruder having a screw of 40 mm$\phi$. The pellet showed MI of 0.32 and FR of 75. The number of gels in the film was more than 10000. ESCR was only 2 hours.

COMPARATIVE EXAMPLE B

A catalyst was prepared as follows in accordance with the disclosure of Japanese Patent Application Laid Open No. 24291/1977 and polymerization using said catalyst was carried out in order to compare with the present catalyst.

(I-a) Synthesis of the solid component (a)

Oxygen gas and chlorine gas were passed through a catalyst HgO distributed on the surface of glass wool to obtain dichlorine monoxide $Cl_2O$, the procedure being carried out carefully because the reaction and the product are very dangerous and poisonous. Dichlorine monoxide $Cl_2O$ was bubbled into titanium tetrachloride, charged in a 500 ml flask purged with nitrogen and maintained at 60° C., at a flow rate of 1 l/min for 5 hours to prepare titanium oxydichloride $TiOCl_2$. $TiOCl_2$ was precipitated from $TiCl_4$ liquid, isolated, washed with n-hexane and dried.

Two hundred ml of titanium tetrachloride containing 31 g of $TiOCl_2$ as a slurry was added dropwise to 300 ml of titanium tetrachloride solution having 31 g of anhydrous aluminum trichloride under a nitrogen atmosphere. After one hour, the mixture changed to a yellow transparent solution.

The solution was cooled to room temperature and allowed to stand overnight. Excess titanium tetrachloride was evaporated from the solution at 100° C. under reduced pressure to obtain a light yellow powder. This powder was used in polymerization as the solid component (a).

(I-b) Synthesis of the solid component (b)

The solid component (b) was synthesized as in (I-b) of Comparative Example A.

(II) Polymerization

Polymerization was carried out under the same conditions as in Example 1, by using 720 mg of the solid component (a), 80 mg of the solid component (b) and 15 mmol of aluminum triisobutyl to give 6.0 Kg of polymer. The polymer powder showed MI of 0.43, FR of 50, a true specific gravity of 0.964 and a bulk density of 0.19.

(III) Moldability

The polymer was pelletized with an extruder having a screw of 40 mm$\phi$. The pellet showed MI of 0.30 and FR of 70. The number of gels in the film was more than 10000. ESCR was only one hour.

EXAMPLE 4

(I) Synthesis of the solid catalyst component

First, a solid (1) was prepared by the same method as described in part (I) of Example 1 except that an octane solution containing 4 mol/l of titanium tetrachloride and isoamyl titanate pentamer were used as titanium tetrachloride and polytitanate, respectively, and except that the reaction was carried out at 130° C. for 5 hours, dropwise addition taking one hour and further reaction 4 hours. The solid (1) analyzed Ti 37.5 wt.% and Cl 40.8 wt.%.

Ten mmol (based on titanium) of the solid (1) and a hexane solution containing 10 mmol (based on magnesium) of the magnesium complex BMg($C_2H_5$)$_{2.5}$(n-$C_4H_9$)$_{1.5}$(On-$C_4H_9$)$_{0.9}$ were reacted under the same conditions described in Example 1 to obtain a solid catalyst component (A).

(II) Polymerization

In a 1.5 l autoclave, evacuated and nitrogen filled, were placed 80 mg of the solid catalyst component (A) and 0.4 mmol of aluminum triisobutyl with 0.8 l of hexane previously dehydrated and degassed. While keeping the internal temperature of the autoclave at 85° C., hydrogen was added up to 5 Kg/cm$^2$. While maintaining the total gauge pressure of 10 Kg/cm$^2$ by adding additional ethylene, the polymerization was carried out for 2 hours. The yield of polymer was 240 g. The polymer powder showed MI of 0.58 and FR of 75.

EXAMPLE 5

(I) Synthesis of the solid catalyst component

A solid (1) was synthesized as in Example 1, except that an octane solution containing 4 mol/l of titanium tetrachloride and tert-butyl titanate dimer were used as titanium tetrachloride and polytitanate respectively, and that the reaction was run at 130° C. for 5 hours.

The solid (1) obtained had Ti of 35.8 wt.% and Cl of 39.1 wt.%.

Ten mmol (based on titanium) of the solid (1) and a hexane solution containing 10 mmol (based on magnesium) of the magnesium complex AlMg$_{2.0}$($C_2H_5$)$_{2.0}$(n-$C_4H_9$)$_{4.0}$[(OSiH.($CH_3$).($C_2H_5$)] 1.0 were reacted under the same reaction conditions described in Example 1 to prepare a solid catalyst component (A).

(II) Polymerization

Polymerization was carried out under the same polymerization conditions as in Example 4, by using 80 mg of the solid catalyst component (A) and 0.4 mmol of aluminum diethyl hydride to give 270 g of a polymer. The polymer powder showed MI of 0.70 and FR of 78.

EXAMPLE 6

(I) Synthesis of the solid catalyst component

A solid was synthesized in the same manner as in Example 1, except that as a polytitanate, cyclohexyl titanate dimer was used and that the reaction was run at 150° C. for 3 hours, the dropwise addition taking one hour and the further reaction 2 hours. The solid (1) obtained contained Ti 36.2 wt.% and Cl 38.7 wt.%.

Ten mmol (based on titanium) of the solid (1) and a hexane solution containing 10 mmol (based on magnesium) of the organomagnesium complex BeMg$_{3.0}$($C_2H_5$)$_{2.1}$(N-$C_4H_9$)$_{5.9}$ were reacted under the same conditions as in Example 1 to obtain the solid catalyst component (A).

(II) Polymerization

Polymerization was carried out under the same polymerization conditions as in Example 4, by using 80 mg of the solid catalyst component (A) and 1.6 mmol of aluminum trihexyl to give 245 g of a polymer. The polymer powder showed MI of 0.25 and FR of 90.

EXAMPLE 7

(I) Synthesis of the solid catalyst component

A solid (1) was synthesized as described in Example 1, except that as polytitanate sec-butyl titanate pentamer was employed and the reaction was run at 100° C. for 3 hours. The solid (1) obtained contained Ti 37.7 wt.% and Cl 38.3 wt.%.

Ten mmol (based on titanium) of the solid (1) and a methylcyclohexane solution containing 10 mmol of didecyl magnesium were reacted as described in Example 1 to prepare the solid catalyst component (A).

(II) Polymerization

Polymerization was carried out under the same polymerization conditions as in Example 4, by using 80 mg of the solid catalyst component (A) and 1.6 mmol of aluminum isoprenyl to give 200 g of a polymer. The polymer powder showed MI of 0.10 and FR of 105.

EXAMPLE 8

(I) Synthesis of the solid catalyst component

A solid (1) was synthesized as described in Example 1, except that 300 mmol of an octane solution containing 4 mol/l of titanium tetrachloride employed and the reaction was run at 80° C. for 5 hours, the dropwise addition taking one hour and the further reaction 4 hours. The solid (1) obtained contained Ti 37.1 wt.% and Cl 35.5 wt.%.

Ten mmol (based on titanium) of the solid (1) and a hexane solution containing 10 mmol (based on magnesium) of the organomagnesium complex (n-$C_4H_9$)$_2$Mg.1.2$C_4H_4$O were reacted as in Example 1 to prepare the solid catalyst component (A).

(II) Polymerization

Polymerization was carried out under the same polymerization conditions as in Example 4, by using 80 mg of the solid catalyst component (A) and 0.8 mmol of the organoaluminum Al(iso-$C_4H_9$)$_{2.5}$Cl$_{0.5}$ to give 130 g of a polymer. The polymer powder showed MI of 0.91 and FR of 64.

EXAMPLE 9

(I) Synthesis of the solid catalyst component

The solid (1) was synthesized as described in Example 1, except that 10 g of anhydrous MgCl$_2$ was suspended in 700 ml of an octane solution containing 1 mol/l of titanium tetrachloride charged in a 1 l flask and that 100 mmol (based on titanium) of isopropyl titanate decamer was placed in the dropping funnel.

Ten mmol (based on titanium) of the solid (1) obtained and a hexane solution containing 5 mmol (based on magnesium) of the organomagnesium n-$C_4H_9$MgCl.1.1(n-$C_4H_9$)$_2$O were reacted as in Example 1 to prepare the solid catalyst component (A).

(II) Polymerization

Polymerization was carried out under the same polymerization conditions as in Example 4, by using 80 mg of the solid catalyst component (A) and 0.8 mmol of the organoaluminum Al($C_2H_5$)$_{2.5}$(O$C_2H_5$)$_{0.5}$ to give 265 g of a polymer. The polymer powder showed MI of 0.57 and FR of 78.

EXAMPLE 10

(I) Synthesis of the solid catalyst component

A solid (1) was synthesized as described in Example 9, except that 10 g of silica (prepared by FUJI-DAVISON CHEMICAL LTD., Grade 952) was used instead of 10 g of anhydrous $MgCl_2$. Ten mmol (based on titanium) of the solid (1) obtained and a heptane solution containing the organomagnesium complex (sec-$C_4H_9$)Mg(OSiH.$CH_3$.n-$C_4H_9$) were reacted as in Example 1 to prepare the solid catalyst component (A).

(II) Polymerization

Polymerization was carried out under the same polymerization conditions as in Example 4, by using 80 mg of the solid catalyst component (A) and 1.6 mmol (based on magnesium) of the organomagnesium complex $AlMg_{2.0}(C_2H_5)_{3.1}(C_4H_9)_{3.9}$ to prepare 160 g of a polymer. The polymer powder showed MI of 0.43 and FR of 80.

EXAMPLE 11

(I) Synthesis of the solid catalyst component

A solid (1) was synthesized as described in Example 9, except that 10 g of titanium hydroxide was used instead of 10 g of 10 g of anhydrous $MgCl_2$.

Ten mmol (based on titanium) of the solid (1) obtained and a heptane solution containing 3.3 mmol (based on magnesium) of the organomagnesium (sec-$C_4H_9$)Mg(n-$C_4H_9$) were reacted as in Example 1 to prepare the solid catalyst component (A).

(II) Polymerization

Polymerization was carried out under the same polymerization conditions as in Example 4, by using 80 mg of the solid catalyst component (A) and 0.4 mmol of aluminum triisobutyl to give 125 g of a polymer. The polymer powder showed MI of 0.36 and FR of 85.

EXAMPLE 12

(I) Synthesis of the solid catalyst component

A solid (1) was synthesized as described in Example 9, except that 10 g of magnesium oxide was used instead of 10 g of anhydrous $MgCl_2$.

Ten mmol (based on titanium) of the solid (1) obtained and a heptane solution containing 10 mmol (based on magnesium) of the organomagnesium ($C_2H_5$)Mg(n-$C_4H_9$) were reacted as in Example 1 to prepare the solid catalyst component (A).

(II) Polymerization

Polymerization was carried out under the same polymerization conditions as in Example 4, by using 80 mg of the solid catalyst component (A) and 0.4 mmol of aluminum triisobutyl to give 200 g of a polymer. The polymer powder showed MI of 0.14 and FR of 94.

EXAMPLE 13

(I) Synthesis of the solid catalyst component

Ten mmol (based on titanium) of the solid (1) prepared in Example 1 and a hexane solution containing 3.3 mmol (based on magnesium) of the organomagnesium complex $AlMg_{6.0}(C_2H_5)_{2.0}(n-C_4H_9)_{9.5}(On-C_4H_9)_{3.5}$ were reacted as described in Example 1 to prepare the solid catalyst component (A).

(II) Polymerization

Polymerization was carried out under the same polymerization conditions as in Example 4, by using 80 mg of the solid catalyst component (A) and 0.4 mmol of aluminum diisobutyl hydride to give 320 g of a polymer. The polymer powder showed MI of 0.52 and FR of 79.

In the following two Comparative Examples, the solids (1) prepared by the reaction of (i) a polytitanate and (ii) a titanium tetrahalide, without treatment with an organomagnesium solution (2) were employed instead of the solid catalyst component (A).

COMPARATIVE EXAMPLE C

Polymerization was carried out under the same polymerization conditions as in Example 4, by using 80 mg of the solid (1) prepared in Example 1 and 0.4 mmol of aluminum triisobutyl. Only 75 g of polymer was obtained of MI below 0.01.

COMPARATIVE EXAMPLE D

Polymerization was carried out under the same polymerization conditions as in Example 4, by using 80 mg of the solid (1) prepared in Example 2 and 0.4 mmol of aluminum triisobutyl. Only 70 g of polymer was obtained of MI below 0.01.

EXAMPLE 14

Polymerization was carried out using 80 mg of the solid catalyst component (A) prepared in Example 1 and 0.4 mmol of aluminum triisobutyl, and following the same procedure described in Example 4, except that an ethylene-propylene gas mixture containing 4 mol % of propylene was used in place of ethylene. There were obtained 265 g of polymer. The polymer powder showed MI of 1.47, FR of 71 and a true specific gravity of 0.957.

EXAMPLE 15

Polymerization was carried out using the same catalyst employed in Example 14 and following the same polymerization conditions as in Example 14, except that an ethylene-butene-1 gas mixture containing 2 mol% of butene-1 was used in place of the ethylene-propylene gas mixture. There were obtained 245 g of a polymer. The polymer powder showed MI of 1.20, FR of 74 and a true specific gravity of 0.950.

EXAMPLE 16

(I) Synthesis of the solid catalyst component

In a 300 ml glass flask equipped with a condenser and a stirrer and purged with nitrogen were placed 150 ml of a n-decane solution containing 4 mol/l of the titanium compound $(Ti(O-i-C_3H_7)_{0.5}Cl_{3.5}$.

Then the solution was maintained at 110° C. for 3 hours. With the passage of time, a precipitate was formed. The solid portion was isolated, washed with n-hexane and dried to obtain 24.5 g of a solid (1). The content of Ti and Cl in the solid (1) were 37.9 wt.% and 35.9 wt.%, respectively, which corresponded to an atomic ratio Cl/Ti of 1.27, and the content of O-i-$C_3H_7$ was less than 0.1 wt.%.

Ten mmol (based on titanium) of the solid (1) and 100 ml of n-hexane were charged to a 150 ml flask equipped with a dropping funnel and a stirrer, slurried and cooled to $-10°$ C. To the slurry, 50 ml of a n-hexane solution containing 10 mmol (based on magnesium) of the organomagnesium complex AlMg$_{6.0}$(C$_2$H$_5$)$_{2.9}$(n-C$_4$H$_9$)$_{12.1}$ was added dropwise over 30 minutes with stirring at −10° C. for 1.5 hours. The solid catalyst component (A) formed was isolated, washed and dried.

(II) Polymerization

In a 30 l autoclave evacuated and nitrogen filled were placed 800 mg of the solid catalyst component (A) and 7.5 mmol of aluminum triethyl with 15 l of hexane. While keeping the internal temperature of the autoclave at 90° C., hydrogen was added up to 5.5 Kg/cm$^2$. Then ethylene was added up to a total gauge pressure of 10 Kg/cm$^2$. While maintaining the gauge pressure by adding additional ethylene, the polymerization was carried out for 4 hours. The yield of the polymer was 6.2 Kg. The polymer powder showed MI of 0.45, FR of 85, a true specific gravity of 0.966 and a bulk density of 0.45.

(III) Moldability

The polymer obtained was pelletized with an extruder having a screw of 40 mm$\phi$. The pellet showed MI of 0.27 and Fr of 140. The die swell of the polymer is shown in Table 4 along with the data for another polyethylene.

TABLE 4

|  | Polyethylene of Example 16 | Conventional Polyethylene Hi-Zex 6200B | Blended Polyethylene Example 16/6200B = 1/9 |
|---|---|---|---|
| die swell | 65 | 35 | 40 |

The polyethylene obtained in Example 16 itself had a large die swell, and markedly improved that of the other polymer having a small die swell.

Bottles molded therefrom had a good surface appearance and film showed gel numbers of less than 50. This polymer was excellent in ESCR with a value of more than 24 hours.

EXAMPLE 17

(I) Synthesis of the solid catalyst component

The solid (1) was synthesized in the same manner as described in Example 16, except that the titanium compound Ti(O-sec-C$_4$H$_9$)$_{0.5}$Cl$_{3.5}$ was used instead of Ti(O-i-C$_3$H$_7$)$_{0.5}$Cl$_{3.5}$. The solid (1) obtained contained Ti 36.8 wt.% and Cl 37.1 wt.%, and an atomic ratio of Cl/Ti of 1.36.

Ten mmol of the solid (1) and 5 mmol of the organomagnesium complex AlMg$_{3.0}$(C$_2$H$_5$)$_{3.1}$(n-C$_4$H$_9$)$_{5.9}$ were reacted at 20° C. for 3 hours in the same manner as described in Example 16 to obtain the solid catalyst component (A).

(II) Polymerization

Polymerization was carried out under the same polymerization conditions as in Example 16, by using 800 mg of the solid catalyst component (A) and 30 mmol of aluminum trinormalbutyl to give 5.8 Kg of polymer. The polymer powder showed MI of 0.30, FR of 90, a true specific gravity of 0.964 and a bulk density of 0.43.

(III) Moldability

The polymer was pelletized with an extruder having a screw of 40 mm$\phi$. The pellet obtained showed MI of 0.21 and FR of 125. Die swell is shown in Table 5 with the data for another polymer.

Bottles molded from the product had a good surface appearance. The number of gels was less than 50 and the ESCR of this polymer was more than 24 hours.

TABLE 5

|  | Polyethylene of Example 17 | Conventional Polyethylene Hi-Zex 6200B | Blended Polyethylene Example 17/6200B = 15/85 |
|---|---|---|---|
| die swell | 68 | 35 | 41 |

EXAMPLE 18

(I) Synthesis of the solid catalyst component

The solid (1) was synthesized in the same manner as described in Example 16, except that the titanium compound Ti(O-tert-C$_4$H$_9$)$_{0.5}$Cl$_{3.5}$ was used instead of Ti(O-i-C$_3$H$_7$)$_{0.5}$Cl$_{3.5}$. The solid (1) obtained contained Ti 37.2 wt.%, Cl 35.8 wt.%, and had a radio of Cl/Ti of 1.30.

Ten mmol of the solid (1) and 20 mmol of the organomagnesium complex ZnMg$_{5.0}$(C$_2$H$_5$)$_{2.1}$(C$_6$H$_{13}$)$_{10}$ were reacted at −30° C. for 4 hours in the same manner as described in Example 16 to obtain the solid catalyst component (A).

(II) Polymerization

Polymerization was carried out under the same polymerization conditions as in Example 16, by using 800 mg of the solid catalyst component (A) and 30 mmol of aluminum triisobutyl to prepare 5.8 Kg of polymer. The polymer powder showed MI of 0.10, FR of 98, a true specific gravity of 0.960 and a bulk density of 0.44.

(III) Moldability

Die swell was measured by the same method described in Example 16. Results were as given in Table 6. Film from the polymer had a gel number of less than 50 and was excellent in tenacity. At the extrusion die there was a good bubble-stability.

TABLE 6

|  | Polyethylene of Example 18 | Conventional Polyethylene Hi-Zex 7000F | Blended Polyethylene Example 18/7000F = 15/85 |
|---|---|---|---|
| die swell | 59 | 31 | 38 |

EXAMPLE 19

(I) Synthesis of the solid catalyst component

The solid (1) was synthesized in the same manner as described in Example 16, except that the titanium compound Ti(O-sec-C$_5$H$_{11}$)$_{0.5}$Cl$_{3.5}$ was used instead of Ti(O-i-C$_3$H$_7$)$_{0.5}$Cl$_{3.5}$. The solid (1) obtained contained Ti 34.5 wt% and Cl 36.1 wt%.

Ten mol of the solid (1) and 10 mmol of the organomagnesium complex BMg$_9$(C$_2$H$_5$)$_{2.6}$(n-C$_4$H$_9$)$_{9.9}$(O-n-C$_4$H$_9$)$_{8.5}$ were reacted in the same manner as described in Example 16 to obtain the solid catalyst component (A).

(II) Polymerization

In a 1.5 l autoclave, evacuated and nitrogen-filled, were placed 80 mg of the solid catalyst component (A) and 0.4 mmol of aluminum triisobutyl with 0.8 l of hexane previously dehydrated and degassed. While keeping the internal temperature of the autoclave at 90° C., hydrogen was added up to 5 Kg/cm$^2$. Then ethylene was added up to a total gauge pressure of 10 Kg/cm$^2$.

While maintaining the total gauge pressure of 10 Kg/cm$^2$ by adding ethylene, polymerization was carried out for 3 hours. The yield of polymer was 340 g. The polymer powder showed MI of 0.75 and FR of 70.

EXAMPLE 20

(I) Synthesis of the solid catalyst component

The solid (1) was synthesized in the same manner as described in Example 16, except that the titanium compound Ti(O-sec-C$_6$H$_{13}$)$_{0.5}$Cl$_{3.5}$ was used instead of Ti(O-i-C$_3$H$_7$)$_{0.5}$Cl$_{3.5}$. The solid (1) obtained contained Ti 37.5 wt.% and Cl 36.5 wt.%.

Ten mmol of the solid (1) and 10 mmol of the organomagnesium complex AlMg$_{2.0}$(C$_2$H$_5$)$_{2.0}$(n-C$_4$H$_9$)$_{4.0}$(OSiH.CH$_3$.C$_2$H$_5$)$_{1.0}$ were reacted in the same manner as described in Example 16 to obtain the solid catalyst component (A).

(II) Polymerization

Polymerization was carried out under the same polymerization conditions as in Example 19, by using 80 mg of the solid catalyst component (A) and 0.4 mmol of aluminum diisobutyl hydride to give 320 g of a polymer. The polymer powder showed MI of 0.25 and FR of 86.

EXAMPLE 21

(I) Synthesis of the solid catalyst component

The solid (1) was synthesized in the same manner as described in Example 16, except that the titanium compound Ti(O-C$_6$H$_{11}$)$_{0.5}$Cl$_{3.5}$ was used instead of Ti(O-i-C$_3$H$_7$)$_{0.5}$Cl$_{3.5}$. The solid (1) obtained contained Ti 38.0 wt.% and Cl 37.5 wt.%.

Ten mmol of the solid (1) and 10 mmol of the organomagnesium complex BeMg$_{3.0}$(C$_2$H$_5$)$_{2.1}$(N-C$_4$H$_9$)$_{5.9}$ were reacted in the same manner as described in Example 16 to obtain the solid catalyst component (A).

(II) Polymerization

Polymerization was carried out under the same polymerization conditions as in Example 19, by using 80 mg of the solid catalyst component (A) and 0.8 mmol of aluminum trioctyl to give 280 g of a polymer. The polymer powder showed MI of 0.55 and FR of 75.

EXAMPLE 22

(I) Synthesis of the solid catalyst component

The titanium compound Ti(O-i-C$_3$H$_7$)Cl$_3$ was reacted at 150° C. for 4 hours in the same manner as described in Example 16 to obtain the solid (1). The Ti and Cl contents in the solid (1) were 38.4 wt% and 34.8 wt.%, respectively.

Ten mmol of the solid (1) and 10 mmol of didecyl magnesium were reacted under the same conditions as in Example 16 to obtain the solid catalyst component (A).

(II) Polymerization

Polymerization was carried out under the same polymerization conditions as in Example 19, by using 80 mg of the solid catalyst component (A) and 1.6 mmol of aluminum isoprenyl to give 210 g of a polymer. The polymer powder showed MI of 0.18 and FR of 102.

EXAMPLE 23

(I) Synthesis of the solid catalyst component

The titanium compound Ti(O-i-C$_3$H$_7$)$_{0.75}$Cl$_{3.25}$ was reacted at 130° C. for 4 hours in the same manner as described in Example 16 to obtain the solid (1). The Ti and Cl contents in the solid (1) were 37.9 wt.% and 35.6 wt.%, respectively.

Ten mmol of the solid (1) and 10mmol of the organomagnesium complex (n-C$_4$H$_9$)$_2$Mg.1.2C$_4$H$_4$O were reacted under the same conditions as in Example 16 to obtain the solid catalyst component (A).

(II) Polymerization

Polymerization was carried out under the same polymerization conditions as in Example 19, by using 80 mg of the solid catalyst component (A) and 0.8 mmol of the aluminum compound AlBu$_{2.5}$Cl$_{0.5}$ to give 240 g of a polymer. The polymer powder showed MI of 0.87 and FR of 68.

EXAMPLE 24

(I) Synthesis of the solid catalyst component

A n-decane solution (150 ml) containing 1.0 mol/l of the titanium compound Ti(O-i-C$_3$H$_7$)$_{0.35}$Cl$_{3.65}$ was reacted in the presence of 10 g of anhydrous MgCl$_2$ at 150° C. for 4 hours in the same manner as described in Example 16. A solid portion was isolated, washed with n-hexane and dried to obtain the solid (1).

Ten mmol (based on titanium) of the solid (1) and 5 mmol of the organomagnesium compound n-C$_4$H$_9$MgCl.1.1(n-C$_4$H$_9$)$_2$O were reacted in the same manner as described in Example 16 to obtain the solid catalyst component (A).

(II) Polymerization

Polymerization was carried out under the same polymerization conditions as in Example 19, by using 100 mg of the solid catalyst component (A) and 0.8 mmol of the organoaluminum Al(C$_2$H$_5$)$_{2.5}$(OC$_2$H$_5$)$_{0.5}$ to give 330 g of a polymer. The polymer powder showed MI of 0.15 and FR of 95.

EXAMPLE 25

(I) Synthesis of the solid catalyst component

A n-decane solution (50 ml) containing 1.0 mol/l of the titanium compound Ti(O-i-C$_3$H$_7$)$_{0.25}$Cl$_{3.75}$ was reacted in the presence of 10 g of silica (prepared by FUJI-DAVISON CHEMICAL LTD., Grade 952) at 130° C. for 4 hours in the same manner as described in Example 16. A solid portion was isolated, washed with n-hexane and dried to obtain the solid (1).

Ten mmol (based on titanium) of the solid (1) and 5 mmol of the organomagnesium compound n-C$_4$H$_9$Mg(O-SiH.CH$_3$.n-C$_4$H$_9$) were reacted at −10° C. for 2 hours in the same manner as described in Example 16 to obtain the solid catalyst component (A).

(II) Polymerization

Polymerization was carried out under the same polymerization conditions as in Example 19, by using 100 mg of the solid catalyst component (A) and 0.8 mmol of the organoaluminum AlMg$_{2.0}$(C$_2$H$_5$)$_{3.1}$(n-C$_4$H$_9$)$_{3.9}$ to give 310 g of a polymer. The polymer powder showed MI of 0.36 and FR of 83.

EXAMPLE 26

(I) Synthesis of the solid catalyst component

A solid (1) was prepared by heating 150 ml of the titanium compound Ti(O-i-C$_3$H$_7$)$_{0.25}$Cl$_{3.75}$ at 80° C. for 3 hours.

The Ti and Cl contents in the solid (1) were 38.2 wt.% and 36.2 wt.%, respectively.

Ten mmol (based on titanium) of the solid (1) and 10 mmol of the organomagnesium n-$C_4H_9MgC_2H_5$ were reacted in the same manner as described in Example 16 to obtain the solid catalyst component (A).

(II) Polymerization

Polymerization was carried out under the same polymerization conditions as in Example 19, by using 80 mg of the solid catalyst component (A) and 1.6 mmol of $Al(C_6H_{13})_3$ to give 280 g of a polymer. The polymer powder showed MI of 0.82 and FR of 82.

EXAMPLE 27

(I) Synthesis of the solid catalyst component

To 150 ml of a n-decane solution containing 4 mol/l of $TiCl_4$, 50 ml of n-decane solution of 60 mmol of $Al(O-i-C_3H_7)_3$ was added dropwise for one hour at 100° C. and allowed to react for 2 hours to obtain the solid (1) which contained Ti 36.8 wt.% and Cl 35.9 wt.%.

Ten mmol (based on titanium) of the solid (1) and 10 mmol of sec-$C_4H_9Mgn-C_4H_9$ were reacted in the same manner as in Example 16 to obtain a solid catalyst component (A).

(II) Polymerization

Polymerization was carried out under the same polymerization conditions as in Example 19, by using 80 mg of the solid catalyst component (A) and 0.8 mmol of $Al(i-C_4H_9)_3$ to give 305 g of a polymer. The polymer powder showed MI of 0.42 and FR of 92.

EXAMPLE 28

(I) Synthesis of the solid catalyst component

To 150 ml of n-decane solution containing 4 mol/l of $TiCl_4$, 50 ml of n-decane solution containing 200 mmol of sec-BuOH was added dropwise at 100° C. for one hour and allowed to react further for 2 hours to give a solid (1) which contained Ti of 36.8 wt.% and Cl 37.4 wt.%.

Ten mmol of the solid (1) and 10 mmol of the organomagnesium complex $AlMg_{6.0}(C_2H_5)_{2.9}(n-C_4H_9)_{12.1}$ were reacted in the same manner as in Example 16 to give a solid catalyst component (A).

(II) Polymerization

Polymerization was carried out under the same polymerization conditions as in Example 19, by using 80 mg of the solid catalyst component (A) and 0.4 mmol of $Al(C_2H_5)_3$ to give 320 g of a polymer. The polymer powder showed MI of 0.44 and FR of 85.

COMPARATIVE EXAMPLE E

By using 80 mg of the solid (1) prepared in Part (I) Of Example 16 instead of the solid catalyst component (A) prepared in Example 16 and 0.4 mmol of $Al(C_2H_5)_3$, polymerization was carried out under the same conditions as in Example 19 to give only 78 g of a polymer. The polymer powder showed MI of below 0.01.

COMPARATIVE EXAMPLE F (I) Synthesis of the solid catalyst component

A n-decane solution (150 ml) containing 4 mol/l of the titanium compound $Ti(O-i-C_3H_7)_{1.5}Cl_{2.5}$ was treated under the same reaction conditions as in Example 16 to obtain a solid (1) which contained Ti 41.5 wt.% and Cl 32.2 wt.%.

Ten mmol of the solid (1) and 10 mmol of the organomagnesium complex used in Example 1 were reacted at −10° C. for 2 hours to obtain the solid catalyst component (A).

(II) Polymerization

Polymerization was carried out under the same polymerization conditions as in Example 19, by using 80 mg of the solid catalyst component (A) and 0.4 mmol of $Al(C_2H_5)_3$. There were obtained 35 g of a polymer. The polymer powder showed MI of 0.11.

EXAMPLE 29

Polymerization was carried out using 80 mg of the solid catalyst component (A) prepared in Example 16 and 0.4 mmol of aluminum triethyl, and following the same procedure described in Example 19, except that an ethylene-propylene gas mixture containing 4 mol % of a propylene was used in place of ethylene. There were obtained 330 g of a polymer. The polymer powder showed MI of 1.53, FR of 72 and a true specific gravity of 0.958.

EXAMPLE 30

Polymerization was carried out using the same catalyst employed in Example 29 and following the same polymerization conditions as in Example 29, except that an ethylene-butene-1 gas mixture containing 2 mol % of butene-1 was used in place of the ethylene-propylene gas mixture. There were obtained 310 g of a polymer. The polymer powder showed MI of 1.35, FR of 75 and a true specific gravity of 0.950.

It will be appreciated that the instant specification and examples are set forth by way of illustration and not limitation, and that various modifications and changes may be made without departing from the spirit and scope of the present invention.

What is claimed is:

1. A catalyst suitable for preparing polyethylene, comprising a solid catalyst component (A) and an organometal compound (B), the solid catalyst component (A) being prepared by reducing a solid (1) with an organomagnesium solution (2), the solid (1) being obtained by the thermal decomposition of (i) a polytitanate of the general formula $RO + Ti(OR)_2O]_{\overline{n}}R$ and (ii) a titanium tetrahalide $TiX_4$, or by the thermal decomposition of (iii) a titanium compound of the general formula $Ti(OR)_aX_{4-a}$, wherein R each independently is a secondary or tertiary hydrocarbon radical having at least 3 carbon atoms,
X is a halogen atom,
n is at least 2, and
$0 < a \leq 1$, and where for the thermal decomposition
the temperature is at least 40° C.,
the mole ratio of Ti in $TiX_4$ (ii) to Ti in polytitanate (i) is at least 3, and
the concentration of Ti in (i)+(ii) or in (iii) is at least 1 mol/l,
the solid (1) including X and Ti in the proportion of $0 < X/Ti \leq 2$.

2. The catalyst of claim 1, wherein the solid (1) is obtained by the thermal decomposition of (i) and (ii) and R is a sec- or tert-aliphatic hydrocarbon group having 3 to 6 carbon atoms.

3. The catalyst of claim 2, wherein the material being thermally decomposed is (i)+(ii) and the mole ratio of Ti in TiX$_4$ (ii) to Ti in polytitanate (i) is more than 3.

4. The catalyst of claim 2, wherein TiX$_4$ is titanium tetrachloride.

5. The catalyst of claim 1, wherein the solid (1) is obtained by the thermal decomposition of (iii) and R is a sec- or tert-aliphatic hydrocarbon group having 3 to 6 carbon atoms.

6. The catalyst of claim 5, wherein $0 < a \leq 0.75$.

7. The catalyst of claim 1, wherein in the thermal decomposition the concentration of Ti is at least 4 mol/l and the temperature is at least 80° C.

8. The catalyst of claim 1, wherein X is a chlorine atom.

9. The catalyst of claim 1, wherein the organomagnesium solution (2) is an inert hydrocarbon solvent having dissolved therein an organomagnesium compound or complex having a Mg-C bond.

10. The catalyst of claim 9, wherein the organomagnesium compound or complex is of the formula $M_\alpha Mg_\beta R_p^8 R_q^9 Y_r^1 Y_s^2$ wherein M is aluminum, zinc, boron, lithium or beryllium, $R^8$ and $R^9$ each independently is a hydrocarbon group having 1 to 10 carbon atoms, $Y^1$ and $Y^2$ each independently is $OR^{10}$, $OSiR^{11}R^{12}R^{13}$, $NR^{14}R^{15}$ or $SR^{16}$, $R^{10}$ and $R^{16}$ are hydrocarbon groups having 1 to 10 carbon atoms, $R^{11}$, $R^{12}$, $R^{13}$, $R^{14}$ and $R^{15}$ each independently is hydrogen or a hydrocarbon radical having 1 to 10 carbon atoms, $\alpha$ and $\beta$ are more than zero, p, q, r and s each independently $\geq 0$, m is the valence of M, $p+q+r+s=m\alpha+2\beta$, $\beta/\alpha \geq 0.5$ and $0 \leq (r+s)/(\alpha+\beta) \leq 1.0$.

11. The catalyst of claim 1, wherein the organometal compound (B) is an organoaluminum compound or an organomagnesium complex.

* * * * *